United States Patent

Cheetham et al.

Patent Number: 6,066,311
Date of Patent: May 23, 2000

[54] PRODUCTION AND USES OF CAFFEIC ACID AND DERIVATIVES THEREOF

[75] Inventors: Peter S. J. Cheetham; Nigel E. Banister, both of Canterbury, United Kingdom

[73] Assignee: Zylepsis Limited, Ashford, United Kingdom

[21] Appl. No.: 08/750,227

[22] PCT Filed: Jun. 7, 1995

[86] PCT No.: PCT/GB95/01324

§ 371 Date: Mar. 14, 1997

§ 102(e) Date: Mar. 14, 1997

[87] PCT Pub. No.: WO95/33706

PCT Pub. Date: Dec. 14, 1995

[30] Foreign Application Priority Data

Jun. 8, 1994 [GB] United Kingdom .................... 9411539
Apr. 10, 1995 [GB] United Kingdom .................... 9507415

[51] Int. Cl.$^7$ ............................ A01K 7/44; C07C 229/00
[52] U.S. Cl. ................................ 424/60; 424/59; 560/38; 560/60; 560/75
[58] Field of Search .................... 424/60, 59; 560/38, 560/60, 75

[56] References Cited

U.S. PATENT DOCUMENTS 2,213,717  9/1940  Poizat et al. ............................ 260/473

FOREIGN PATENT DOCUMENTS

| 0272576 | 6/1988 | European Pat. Off. . |
|---|---|---|
| 272576 | 6/1988 | European Pat. Off. . |
| 0350314 | 10/1990 | European Pat. Off. . |
| 2390160 | 5/1978 | France . |
| 2721394 | 11/1978 | Germany . |
| 62-120312 | 6/1987 | Japan . |
| 63-284116 | 11/1988 | Japan . |
| 63-284117 | 11/1988 | Japan . |
| 63-284118 | 11/1988 | Japan . |
| 63-284119 | 11/1988 | Japan . |
| 1013018 | 1/1989 | Japan . |
| 06199649 | 7/1994 | Japan . |
| 06287105 | 10/1994 | Japan . |

OTHER PUBLICATIONS

Ellis, B. E., and Amrhein, N., The 'NIH–Shift' During Aromatic OrthoHydroxylation in Higher Plants, *Phytochemistry*, 10, pp. 3069–3072, 1971, Pergamon Press.

Freudenberg Karl, *Berichte der Deutschen Chemischen Gesellschaft*, vol. 53, No. 1, 1920 Weinheim DE, pp. 232–239. In German—See Ref. AK.

Gestentner B., and Conn, Eric E., "The 2–Hydroxylation of trans–Cinnamic Acid by Chloroplasts from *Melilotus alba* Desr." *Archives of Biochemistry and Biophysics*, 163, pp. 617–624, 1974, Academic Press.

Sripad, G., Prakash, V., Narasinga Rao, M.S. "Extractability of polyphenols of sunflower seed in various solvents.", *J. Biosci*, 4, No. 2, pp. 145–152, 1982.

Tranchino L., Constantino R., and Sodini G., "Food grade oilseed protein processing; sunflower and rapeseed.", *Qual.Plant Foods Hum. Nutr.*, 32, pp. 305–334, 1983.

International Search Report for PCT GB95/01324. which cites References AA, AB, AE, AG and which is in the possession of the USPTO per attached Form PCT/DO/EO/903 dated Jun. 18, 1997.

CA 108:19241 (1987).

Shaku, M. et al. "Efficacy of Sodium Isoferulate as a New Sunscreen Agent", *J. SCCJ*, 26 (1), pp 8–17, (1992).

*Primary Examiner*—Paul J. Killos
*Attorney, Agent, or Firm*—Bromberg & Sunstein LLP

[57] ABSTRACT

There is disclosed a novel method of producing caffeic acid in large quantities, comprising the esterification of chlorogenic acid with an esterifying enzyme. Caffeic acid and its derivatives, produced by this method, may be used in sunscreen compositions, the caffeic acid and its derivatives absorbing both uvA and uvB light.

46 Claims, 8 Drawing Sheets

| Figure 2: HEXANOL ESTER OF CAFFEIC ACID 20µg ml$^{-1}$ IN TLC SOLVENT(HEXANE : ETHANOL, 3:1, & 2% v/v ACETIC ACID) | | |
|---|---|---|
| PEAK No. | 2 | 3 |
| WAVELENGTH (nm) | 251 | 330 |
| ABSORBANCE | 1.016 | 1.747 |
| M.A.V. | 13411 | 23060 |
| $E^{1\%}_{1cm}$ | 508 | 873.5 |

FOR A MOLAR SOLUTION:
TOTAL U.V. ABSORBANCE 285 - 450 nm = 1499520 ABS nm

| Figure 3 : SOLTAN SUNCREAM 0.1% v/v IN ETHANOL | | |
|---|---|---|
| PEAK No. | 1 | 2 |
| WAVELENGTH (nm) | 206 | 311 |
| ABSORBANCE | 1.530 | 1.945 |

| Figure 4 : SOLTAN SUNCREAM 0.1% v/v + CAFFEIC ACID 0.002% v/v IN ETHANOL | | | |
|---|---|---|---|
| PEAK No. | 1 | 2 | 3 |
| WAVELENGTH (nm) | 222 | 235 | 314 |
| ABSORBANCE | 2.131 | 1.990 | 2.540 |

| DMCA 0.001% w/v IN ETHANOL | | |
|---|---|---|
| PEAK No. | 1 | 2 |
| WAVELENGTH (nm) | 284 | 309 |
| ABSORBANCE | 0.778 | 0.737 |
| M.A.V. | 16182 | 15330 |
| $E^{1\%}_{1cm}$ | 778 | 737 |
| FOR A MOLAR SOLUTION: TOTAL U.V. ABSORBANCE 290 - 450 nm = $7.3 \times 10^5$ ABS nm | | |
| FOR A 1% w/v SOLUTION: TOTAL U.V. ABSORBANCE 290 - 450 nm = $3.5 \times 10^4$ ABS nm | | |

| DMCA PHENYL ESTER 0.001% w/v IN ETHANOL | | |
|---|---|---|
| PEAK No. | 1 | 2 |
| WAVELENGTH (nm) | 300 | 328 |
| ABSORBANCE | 0.563 | 0.741 |
| M.A.V. | 15989 | 21044 |
| $E^{1\%}_{1cm}$ | 563 | 741 |
| FOR A MOLAR SOLUTION: | | |
| TOTAL U.V. ABSORBANCE 290 - 450 nm = $11.5 \times 10^5$ ABS nm | | |
| FOR A 1% w/v SOLUTION: | | |
| TOTAL U.V. ABSORBANCE 290 - 450 nm = $4.1 \times 10^4$ ABS nm | | |

| DMCA HEXYL ESTER 0.001% w/v IN ETHANOL | | |
|---|---|---|
| PEAK No. | 1 | 2 |
| WAVELENGTH (nm) | 295 | 322 |
| ABSORBANCE | 0.52 | 0.624 |
| M.A.V. | 15184 | 18221 |
| $E_{1cm}^{1\%}$ | 520 | 624 |
| FOR A MOLAR SOLUTION: TOTAL U.V. ABSORBANCE 290 - 450 nm = 9.6 x $10^5$ ABS nm | | |
| FOR A 1% w/v SOLUTION: TOTAL U.V. ABSORBANCE 290 - 450 nm = 3.3 x $10^4$ ABS nm | | |

PRODUCTION AND USES OF CAFFEIC ACID AND DERIVATIVES THEREOF

THIS INVENTION relates to the production and uses of caffeic acid and derivatives thereof, and more particularly to a method of producing caffeic acids and derivatives from chlorogenic acid and uses of caffeic acid and derivatives thereof as sunscreen additives.

As the harmful effects of strong sunlight become more widely publicized and concern grows over the depletion of the ozone layer, the general public is becoming more aware of the harmful effects of atmospheric ultra-violet radiation. In particular, the identification of atmospheric radiation as a major causative agent in skin cancers has increased the demand for effective and economic protection against atmospheric ultra-violet radiation.

Of the three types of ultraviolet radiation, uvA, uvB and uvC, uvC does not penetrate the earth's atmosphere, being absorbed by the ozone layer. Of the two types of ultraviolet radiation that reach the earth's surface, uvB has been identified as the causative agent of skin cancer. Accordingly, the majority of sunscreens currently available concentrate on the reduction of uvB rays contacting the skin. However, uvA has now been identified as a cause of ageing of skin and wrinkling. As such, it is considered preferable to provide sunscreen agents which reduce the harmful effects of both uvA and uvB in sunlight.

Furthermore, with the increase in environmental awareness in the general public, there is an increased requirement for "natural" products, notably biodegradable products, to avoid environmental damage. There is, therefore, a need for such biodegradable "natural" products for use in sunscreens.

Finally, there is a desire in the art to produce sunscreens which not only have the primary function of blocking ultraviolet light but also have the secondary function of caring for the skin to which they are applied. Thus many sunscreens also contain moisturisers and antioxidants as skin care additives.

One of the most used sunscreen agents is octyl methoxycinnamate (p-methoxycinnamate-2-ethylhexylester). This is an oil soluble uvB absorber having a λ max of 308 nms. The majority of commercial sunscreen agents are also oil soluble uvB absorbers.

A water soluble uvB absorber is phenylbenzimadazole sulphonic acid which has a λ max of 302 nms. One of the few known uvA absorbing agents which is commercially used is the oil-soluble menthylanthranilate. Others include the Parsol range (Givaudan-Roure) for example.

At present sunscreens intended to block uvA and uvB light comprise a combination of two different molecules, one to block uvA light and one to block uvB light. This presents great difficulty in formulation because the two different molecules often have very different physico—chemical properties.

Caffeic acid is a molecule of the formula:

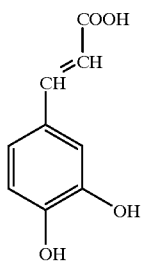

This molecule is known per se but is only of use as a research chemical. It is a natural molecule being found in plants such as coffee. It is extremely difficult and expensive to produce and is available only in very small quantities. At present the method of production of caffeic acid is by solvent extraction from plant tissue and column chromatography. This molecule has now been found to absorb both uvA and uvB. The molecule is, further, biodegradable and has excellent antioxidant properties.

The present invention provides a novel inexpensive method for producing caffeic acid and derivatives thereof. The present invention further allows the use of caffeic acid and derivatives thereof as sunscreen agents.

According to the present invention there is provided a compound of the formula:

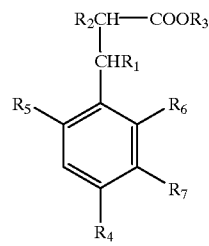

or a salt thereof, wherein $R_1$ is H, OH or $NH_2$, $R_2$ is H, OH or $NH_2$ or $R_1$ and $R_2$ form a double bond, $R_3$ is H, a straight or branched chain, substituted or unsubstituted $C_1$–$C_{16}$ alkyl, alkylene, or alkylyne, a substituted or unsubstituted homocyclic or heterocyclic aromatic group; or a group having a uv absorption extinction coefficient of 2,000 or more, $R_4$, $R_5$ and $R_6$ are H, or an electron donating group, such as OH, $NH_2$, $OCH_3$, SH, $NHCO_2$, OCOH, or a $C_1$ to $C_5$ saturated alkyl group, and $R_7$ is OH or $OCH_3$.

Molecules having a uv absorption extinction coefficient of 2,000 or more include:

5-hydroxyindole radical which has a λ max of 290 nm:

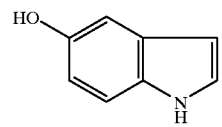

5,6 dihydroxyindole, which absorbs broadly in the uVA region:

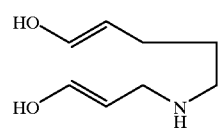

and rutin, which absorbs broadly in the uVA region:

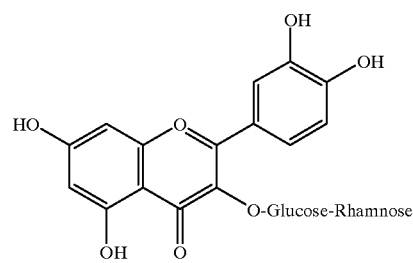

Preferably $R_1$ and $R_2$ form a double bond and $R_3$ is a straight or branched chain unsubstituted $C_1$–$C_{16}$, alkyl, alkylene or alkylyne or a substituted or unsubstituted homocyclic aromatic group. Most preferably $R_3$ is a group of the structure $CH_2=CH_2-R_8$ wherein $R_8$ is a straight or branched chain $C_1-C_{14}$ alkyl. Preferably at least one of $R_4$, $R_5$ and $R_6$ are OH, $NH_2$, $OCH_3$ or a $C_1$ to $C_8$ unsaturated alkyl group.

The caffeic acid ester derivatives which are encompassed by the present invention include the caffeic acid dimer formed by an intermolecular reaction between the COOH of one molecule of caffeic acid and an OH group of another caffeic acid molecule. Other groups encompassed by the definition of $R_3$ in the compound of the present invention include Lawsone (2-hydroxy-1,4-naphthalene dione), and the groups having the structures:

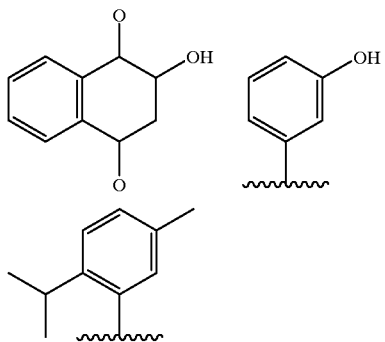

Lawsone not only absorbs ultraviolet light but has a hydroxy group and a double bond suitably positioned to extend directly the conjugated structure of caffeic acid when an ester is formed. Furthermore this molecule is a quinone and, thus, reacts with the tyrosine residues of proteins so as to allow the sunscreen molecule to bind semi-permanently to the surface of the skin.

Other molecules which may be reacted with caffeic acid so as to form esters according to the present invention include allyl alcohol (2-propen-1-ol)

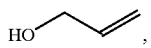, trans-2-hexene-1-ol, which occurs naturally in fruit

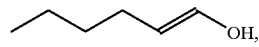, non-cyclic terpene alcohols such as Citronellol:

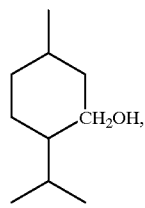

Geraniol:

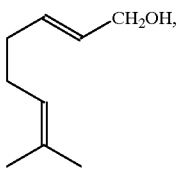

and Nerol

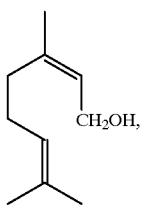

It is envisaged that certain molecules which may form the $R_3$ group of the compound of the present invention may provide the present invention with advantageous properties for inclusion in a sunscreen composition. For instance, two-phenylethanol has a rose aroma:

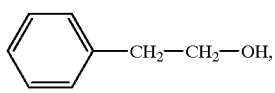

ascorbic acid (vitamin C) has anti-oxidant properties:

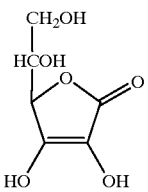

alpha-hydroxy caproic acid has moisturizing properties $$CH_3-(CH_2)_5-\underset{\underset{OH}{|}}{CH}-COOH$$

dihydroxyacetone which is a skin tanning agent $$\begin{array}{c} CH_2OH \\ | \\ C=O \\ | \\ CH_2OH \end{array}$$

L-menthol which has cooling properties and emits a mint aroma

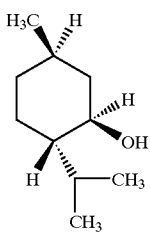

and anthrocyanins are natural plant colours

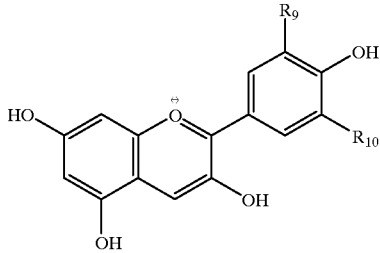

(wherein $R_9$ and $R_{10}$ may be H, OH or $OCH_3$)

It is also possible to combine caffeic acid with a compound of the formula $R_3NH$ so that the $COOR_3$ group of the compound becomes a $CONR_3$ group. Molecules which may be so combined includes sphingosine which is a compound of skin ceramides which provide water-resistant properties:

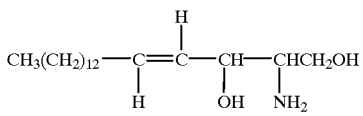

and serine, a naturally occurring amino acid which is a pre-cursor of sphingosine:

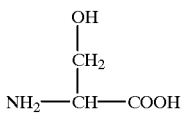

The present invention is not restricted to compounds of the invention when manufactured by the claimed method. An essential aspect of the present invention is the identification of the group of related compounds as very good sunscreen agents. Amongst the compounds of the present invention are dimethoxycinnamic acid and certain derivatives thereof. These are traditionally manufactured by classical chemical means as opposed to enzymatic paths but can be obtained by O-methylation of caffeic acid precursors.

Dimethoxycinnamic acid has a structure:

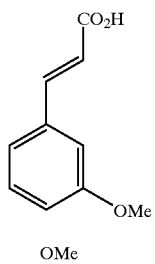

This has a λ max of 309 nms, which is almost perfect for use as a sunscreen. In this respect, the wavelength at which solar radiation has maximum damaging effect on human skin is 308 nms. Furthermore, the uvB absorption of DMCA is comparable to that of octyl methoxycinnamate but, as discussed above, DMCA has additional advantageous uvA adsorption. Furthermore, DMCA and its aliphatic esters, such as the methyl ester:

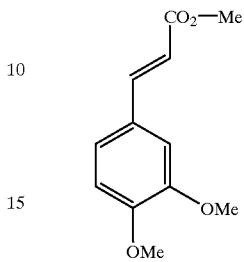

have good antimicrobial activity and superior skin substantitivity properties. These compounds are extracted from natural sources as they are a normal constituent of cereals such as barley.

Simple phenyl esters of dimethoxycinnamic acid, such as:

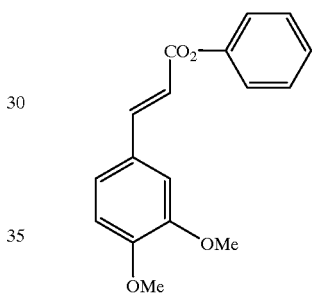

and their substituted derivatives, such as:

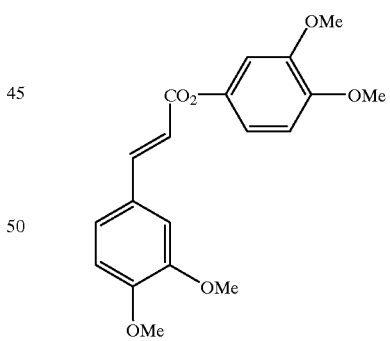

are also of interest as they have a uvA λ max of 328 nms together with an additional uvB absorbence equivalent to about 80% of the uvB absorbence of octyl methoxycinnamate. It should be noted that the sole currently known uvA and B absorber in sunscreens is 3-benzophenone and the dimethoxy cinnamic acid phenyl esters have combined uvA and B absorption significantly greater than that of the 3-benzophenone.

Finally two other derivatives of dimethoxycinnamic acid have been investigated and these have the structures:

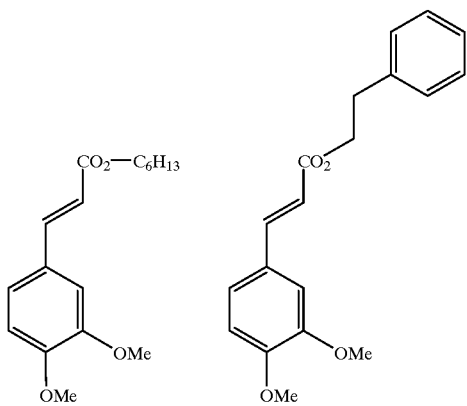

An ideal sun screen molecule should penetrate the outer layer of the skin of the user. The P value of a molecule is a measure of the lipophilicity of the molecule and is measured by measuring its tendency to partition between water and octanol phases in a two-phase mixture. The P value is the relative concentrations of the molecule of interest in water as compared to its concentration in octanol, once equilibrium has been reached. Greatest skin penetration is obtained with molecules having log P value of about 1. Caffeic acid is advantageous in this respect in that the log P value of caffeic acid is about 1. By esterification of caffeic acid to produce esters of the present invention, the compound so manufactured may be tailored so as to modify the log P value of the resulting molecule to provide a required skin penetration property.

According to a further aspect of the present invention there is further provided a method of manufacturing a compound according to the present invention, which method comprises reacting chlorogenic acid with a compound of the formula $R_3OH$, wherein $R_3$ is as defined above, in the presence of a transesterifying enzyme. Chlorogenic acid is a commonly available compound of the formula:

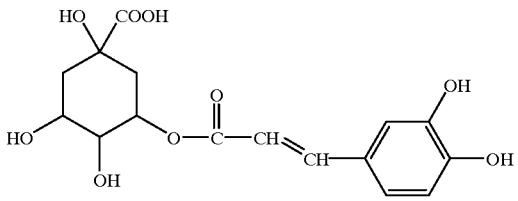

Typical plant sources for chlorogenic acid are sugar cane or tomato.

It is also envisaged that other plant-derived molecules, having the same basic structure as chlorogenic acid, could be reacted with the compound of the formula $R_3OH$ in the presence of a transesterifying enzyme. One such molecule is cynarin ((1α, 3α, 4α, 5β)-1,3-bis[[3-(3,4 dihydroxyphenyl)-1-oxo-2-propenyl]oxy]-4,5-dihydroxycyclohexane carboxylic acid). This molecule, derived from artichokes, has the formula:

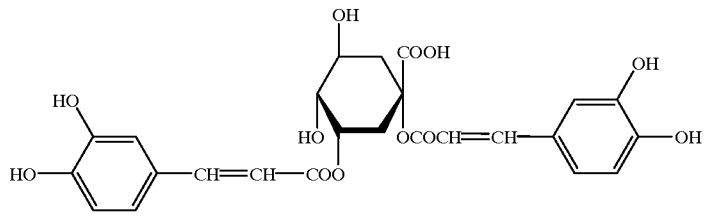

The transesterifying enzyme may be any enzyme which is capable of transesterifying a compound. Such enzymes include hydrolases, esterases, lipases, proteases and glycosidases. Particularly preferred are lipase AP6 (Amino), lipase F4, *A. niger* lipase, most preferably immobilized, porcine pancreatic lipase, *C. antarctica* lipase, porcine liver esterase, chymotrypsin and cellulases.

Caffeic acid may be produced by de-esterification of chlorogenic acid in water, giving rise to caffeic acid and quinic acid as a side product. If the reaction takes place in an organic solvent, esterifying chlorogenic acid with an alcohol, a novel ester derivative is formed by a transesterification reaction, again with quinic acid as a side product. The hydrolytic cleavage may be effected by any of the enzymes listed above as well as pectin-cellulose-and carbohydrate hydrolysing enzymes.

Quinic acid may be converted into benzoquinone using $H_2SO_4$ and $M_nO_2$. Both quinic acid and benzoquinone are useful for the production of chiral intermediates for example as precursors in nucleoside production. Benzoquinone is a precursor of hydroquinone which is widely used in photographic developing solutions. Glycosylation of hydroquinine produces arbutin:

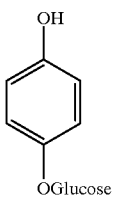

Arbutin, an active compound of garlic, is useful as a skin-lightening agent. Quinic acid may be used to produce hydroquinone dimethylester which may be produced by the esterification of hydroquinone. Hydroquinone dimethylester is commonly found in hyacinth oil and in tea and may be used to perfume products such as soaps.

Furthermore the products of the present invention may be processed by addition of an electron donating group to one or more of the ortho and/or para position on the benzene ring of the core structure of the molecule of the present invention. Examples of electron donating groups are OH, $NH_2$, $OCH_3$, $CH_3$, SH, $NHCO_2H$, OCOH, or a C, to $C_8$ saturated or unsaturated alkyl group. To produce such derivatives, the required ortho position is first hydroxylated according to the process of Ellis and Arheinn, *Phytochemistry*, 10, 3069–3072(1971) or Gestetner and Connee *Arch Biochem Biophys*, 163, 617–627(1974). The hydroxyl group may then be replaced with other electron donating groups by well-known methods, such as those disclosed in *Vogels' Textbook of Practical Organic Chemistry* by A. Vogel (Longman) or *Advanced Organic Chemistry Reaction Mechanisms and Structure, 4th Edition* by J. March (John Wiley & Sons).

According to the present invention there is provided a method of treating a plant residue, which method comprises the step of treating the plant residue with a compound of the formula $R_3OH$, where $R_3$ is as defined above, in the presence of an esterifying enzyme.

The esterifying enzyme may be an esterase, lipase, protease, hydrolase or glycosidase.

There is also provided a method of producing a foodstuff from a plant residue, which method comprises the method, of treating a plant residue, of the present invention. The method of producing a foodstuff from a plant residue may further comprise the step of solvent extraction of caffeic acid and/or derivatives thereof.

Chlorogenic acid is present in many of the plant residues remaining after processing to obtain food materials. For example, it is one of the phenolic components present in sunflower seeds and olives after processing to remove the oils. These residual plant materials are processed as animal feed but the presence of phenolics such as chlorogenic acid reduce the nutritional value of the feed. The phenolics are antinutritional substances whose removal is not easy. Extraction of the chlorogenic acid into aqueous systems is associated with removal of protein so resulting in a loss of nutritional quality; Tranchino. et al, Qual. Plant Plant Foods Hum. Nutr., 1983, 32, 305 for further information, Extraction into organic solvents makes the process logistically inconvenient because of the necessity for sequential extractions, see Sripad et al., J. Biosci., 1982, 4, 145.

The present invention which allows chlorogenic acid and its derivatives to be conveniently hydrolysed results in the production of caffeic acid, a phenolic compound which is easily removed by solvent extraction as described, for example, in Example 1. This therefore allows the easy removal of antinutritional phenolic compounds from animal feedstuff by the use of an enzyme preparation.

According to the present invention there is still further provided a compound of the present invention for use in the prevention of uv light damage to the skin of warm-blooded animals. Yet another aspect of the present invention provides the use of a compound according to the present invention for the manufacture of a medicament for the prevention of uv light damage to the skin of warm-blooded animals.

The present invention also provides a cosmetic method of skin preservation, which method comprises applying to the skin a composition comprising a compound according to the present invention.

There is further provided by the present invention a sunscreen composition, which composition comprises a compound according to the present invention with an adjuvant. The composition may be formulated as a water-in-oil or an oil-in-water mixture. Typical adjuvants include isopropyl myristate, paraffin oil, miglycol, peanut oil, sesame oil, isopropanol and ethanol.

In order to illustrate the features and advantages of the present invention, the present invention will be further described, by way of example only, and with reference to the accompanying drawings, in which.

Figure 1:
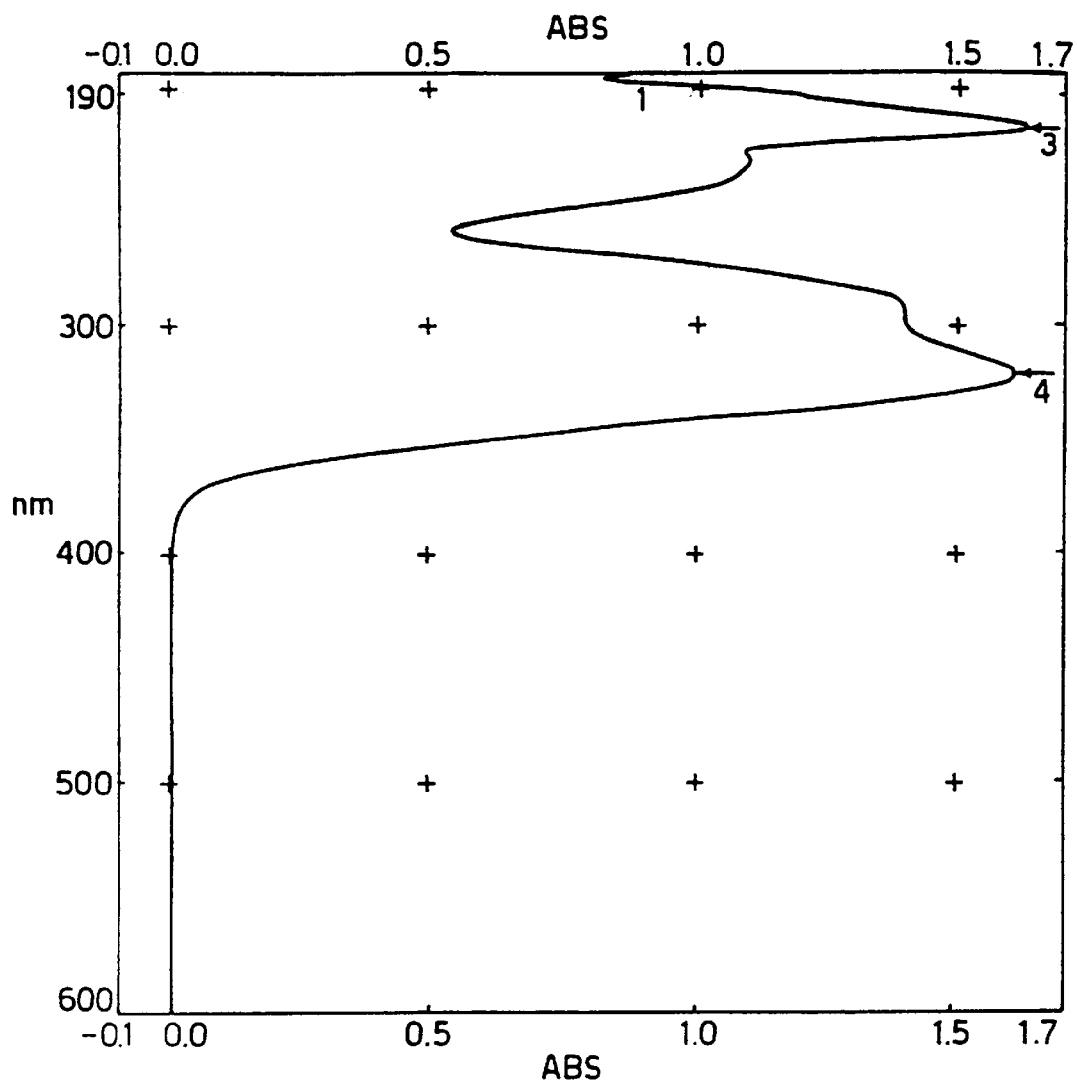
FIG. 1 shows the ultraviolet spectrum of caffeic acid produced by Example 1.

The definition of the values m.a.v. and $E^{1Z}_{1cm}$ are as follows: m.a.v. is the molar absorbence value (E) being the absorbence of a one molar solution of a substance, measured in a 1 cm path length cell at the given wavelength. $E^{1Z}_{1cm}$ is the specific absorbence of a substance, being the absorbence of that substance at 1% concentration in a 1 cm path length cell at the given wavelength. The total uV absorbence is a representation of the area under the curve of the figure usually over the range 285 nm to 450 nm.

EXAMPLE 1

200 mg of chlorogenic acid was added to 10 mls of phosphate buffer (pH6.81). The pH of the solution was adjusted to 7.0 using 1M sodium hydroxide and was, subsequently incubated at 37° C. with 200 mg of immobilized *C. antarctica* lipase. The solution was incubated with the immobilized enzyme for 24 hours, while being shaken at 200 rpm.

At the end of the incubation, the samples were extracted with two equal volumes of diethyl ether. The diethyl ether was added to the sample in a separating funnel and shaken manually for approximately two minutes at room temperature, releasing the pressure from the separating funnel at frequent intervals. The resulting ether layers were pooled, dried over sodium sulphate and subsequently evaporated. The resulting samples were re-suspended in diethyl ether prior to analysis by gas chromatography and thin layer chromatography.

In gas chromatography, 2 microliters of the sample in diethyl ether were injected at a temperature of 300° C. into an A1 Cambridge Model 93 gas chromatograph with an Alltech SE30 column. The carrier gas was at 3.5 bar and the detection temperature was 300° C. The subsequent development in the oven took place for five minutes at 170° C. The temperature was then increased by 10° C. per minute from 170° C. to 290° C. and the temperature was subsequently maintained at 290° C. for five minutes. Caffeic acid was detected by comparison with a standard with a retention time of 5.49 minutes.

In the TLC the samples, dissolved in diethyl ether, were spotted onto Kieselgel $60_2$ $F_{254}$ TLC plates which had been cut to the appropriate size. The solvent, a 3:1 hexane:ethanol mixture+2%V/V acetic acid, was placed in a covered glass container to give a depth of approximately 5 mm. The samples were applied to the TLC plate using drawn capillary tubes and were spotted on to a line approximately 10 mm from the base of the TLC plate. The TLC plate with spotted samples and the appropriate standards (chlorogenic acid, caffeic acid and quinic acid) was placed in the covered TLC tank containing the solvent mixture and was allowed to develop to within approximately 20 mm of the top of the plate. The TLC plate was removed from the TLC tank and the residual solvent was evaporated from the plate by placing it briefly (approx 2 min) in an oven (140° C.). The TLC plate was then visualised by placing it in a container with an atmosphere saturated with iodine until brown spots were seen. Chlorogenic acid and, caffeic acid were visualized as brown spots on the TLC plate. Chlorogenic acid and caffeic acid were identified by comparison to standards of these compounds developed on the TLC plate. The results were as follows:

| Compound | Rf |
|---|---|
| Chlorogenic acid | 0.03 (remains at origin) |
| Caffeic acid | 0.64 |

The uv spectrum of the caffeic acid was taken using a Phillips PU8720 spectrophotometer using a quartz cell (1 cm path length). Absorption spectrum was measured over the range 190 nm to 600 nm wavelengths and a baseline absorption was obtained using an ethanol blank. The absorption spectrum of caffeic acid was obtained by dissolving the appropriate amount of caffeic acid in ethanol to give a solution of 20 ug/ml. The spectrum is shown in FIG. 1. As can be seen, there are high absorbence peaks at 218 nm and 323 nm. Thus, with $\lambda$ max at 218 and 323 nm, caffeic acid is shown to absorb both uvA and uvB light.

EXAMPLE 2

1.246 ml of hexane-1-ol was mixed with 25 ml of hexane. To this was added 600 mg of chlorogenic acid and 200 mg of immobilized *C. antarctica* lipase. The flask was subsequently incubated at 37° C. for 72 hours whilst being shaken at 200 rpm. The immobilized enzyme was removed from the sample by filtration and the organic solvent was subsequently removed by evaporation to dryness. The resulting sample was re-suspended in diethyl ether for analysis by thin layer chromatography.

In the TLC the samples, dissolved in diethyl ether, were spotted onto Kieselgel 60, $F_{254}$ TLC plates which had been cut to the appropriate size. The solvent, a 3:1 hexane:ethanol mixture+2%V/V acetic acid, was placed in a covered glass container to give a depth of approximately 5 mm. The samples were applied to the TLC plate using drawn capillary tubes and were spotted on to a line approximately 10 mm from the base of the TLC plate. The TLC plate with spotted samples and the appropriate standards (chlorogenic acid, caffeic acid and quinic acid) was placed in the covered TLC tank containing the solvent mixture and was allowed to develop to within approximately 20 mm of the top of the plate. The TLC plate was removed from the TLC tank and the residual solvent was evaporated from the plate by placing it briefly (approx 2 min) in an oven (140° C.). The TLC plate was then visualised by placing it in a container with an atmosphere saturated with iodine until brown spots are seen. Chlorogenic acid, and the ester of caffeic acid were visualized as brown spots on the TLC plate. Chlorogenic acid and the ester of caffeic acid were identified by comparison to standards of these compounds developed on the TLC plate. The results were as follows:

| Compound | RF |
|---|---|
| Chlorogenic acid | 0.03 (remains at origin) |
| Hexyl caffeate | 0.45 |

Figure 2:
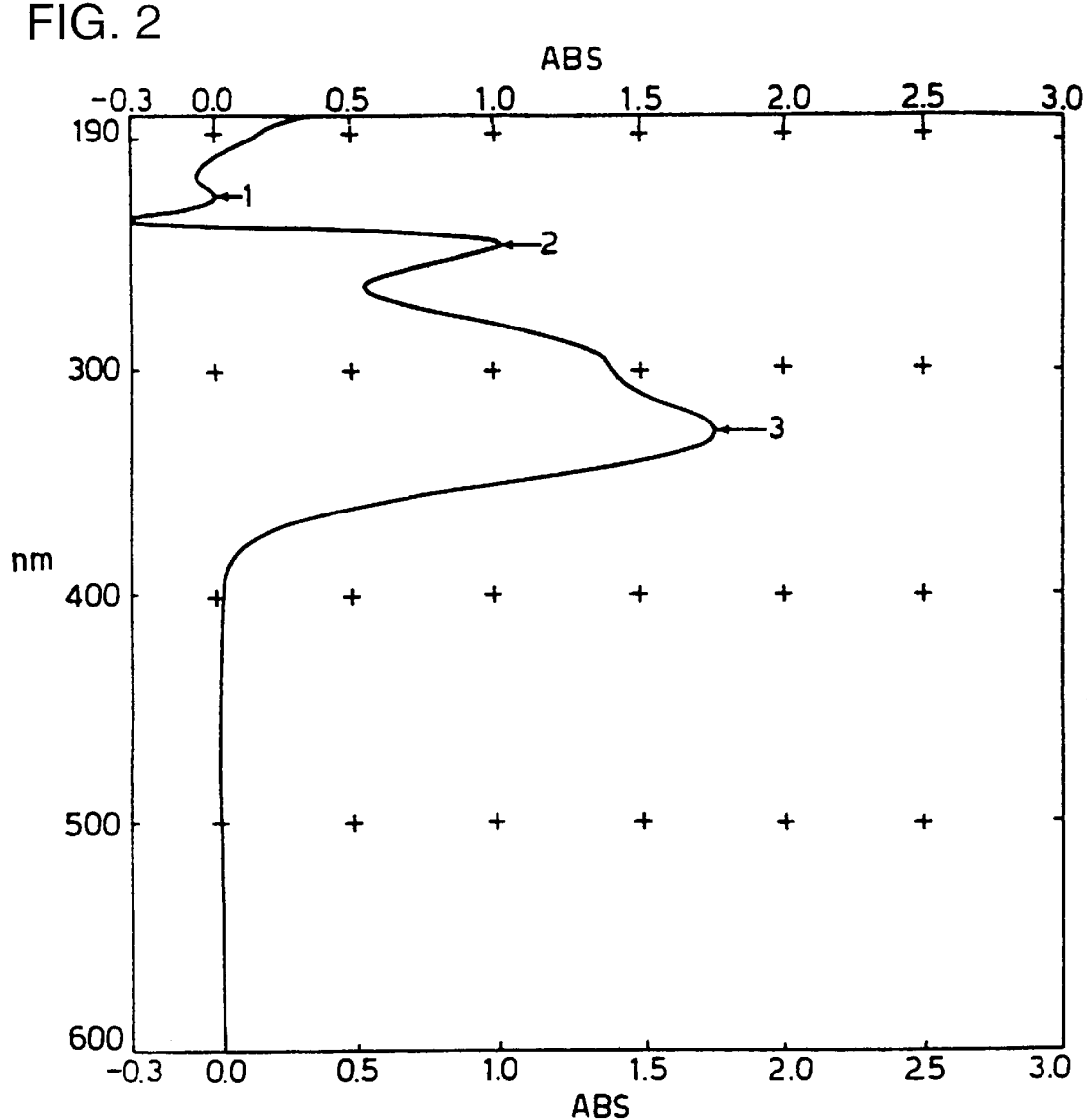
FIG. 2 shows the ultraviolet spectrum of the hexyl caffeate produced in accordance with Example 2.

The uv spectrum of the hexyl caffeate was subsequently determined as in Example 1 and is shown in FIG. 2. As can be seen, the maximum absorption peaks may be found at 251 nm and 330 nm. As such, with a $\lambda$ max at 251 nm and 330 nm, this material absorbs both uvA and uvB light. Furthermore, a comparison with FIG. 1 shows a greater absorbence of uvA and uvB light than caffeic acid.

EXAMPLE 3

To determine the advantageous uv absorption qualities of caffeic acid, steps were taken to determine the advantageous effects of the addition caffeic acid to a commercially available sunscreen.

To 1 g of SOLTAN SPF6™, a commercially available sunscreen, 20 mg of caffeic acid were added to give a final concentration of 2% by weight. The resulting composition was mixed to dissolve the caffeic acid and to provide a uniform dispersion of the caffeic acid. The resultant paste was diluted 1:1000 in ethanol and the uv spectrum of the mixture was determined as in Example 1. The spectrum of the mixture is shown in FIG. 4.

The uv spectrum of SOLTAN alone was measured, for comparison purposes, as in Example 1. This spectrum is shown in FIG. 3.

Figure 3:
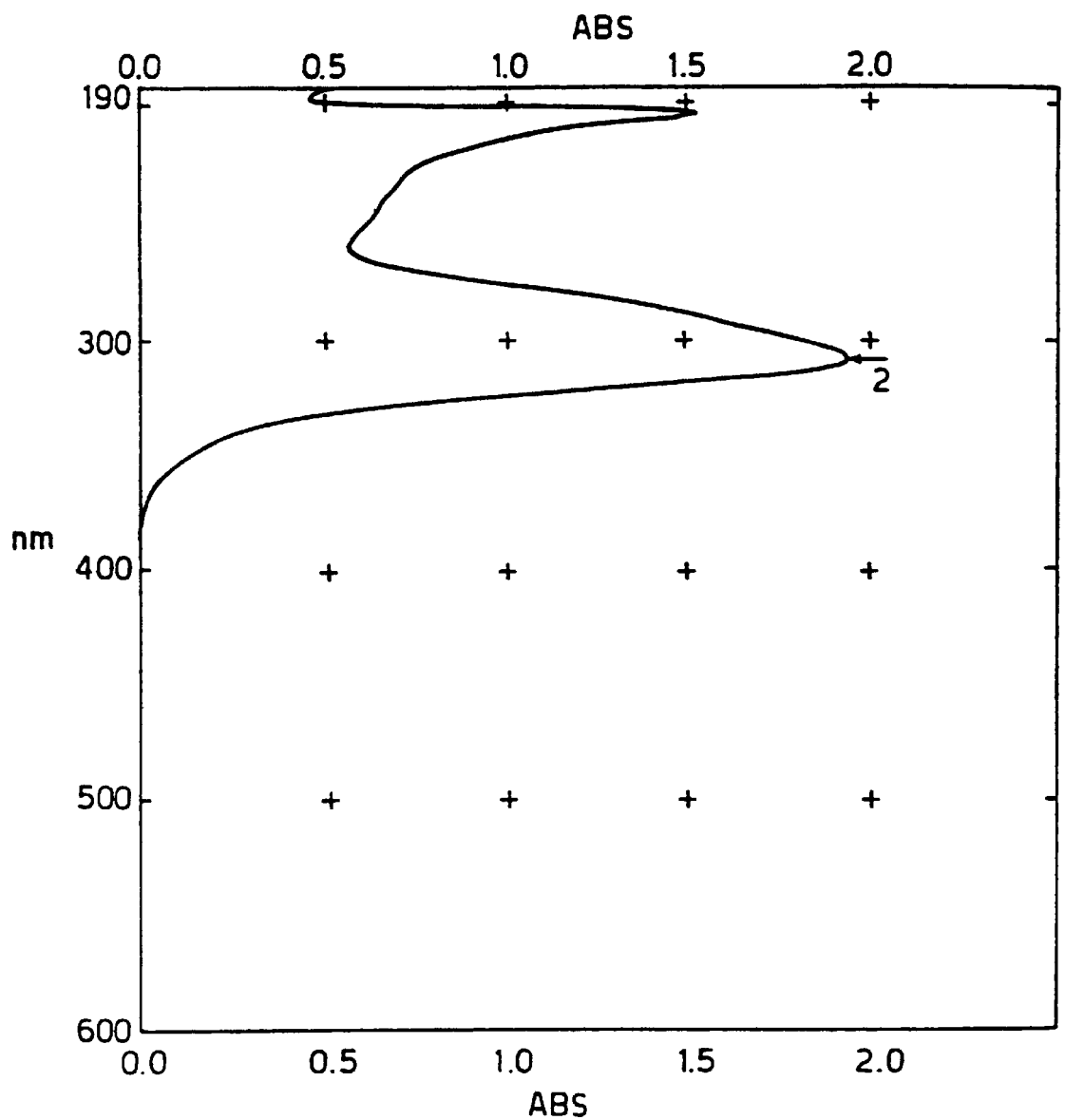
FIG. 3 shows the ultraviolet spectrum of SOLTAN™, a commercially available sunscreen product.
Figure 4:
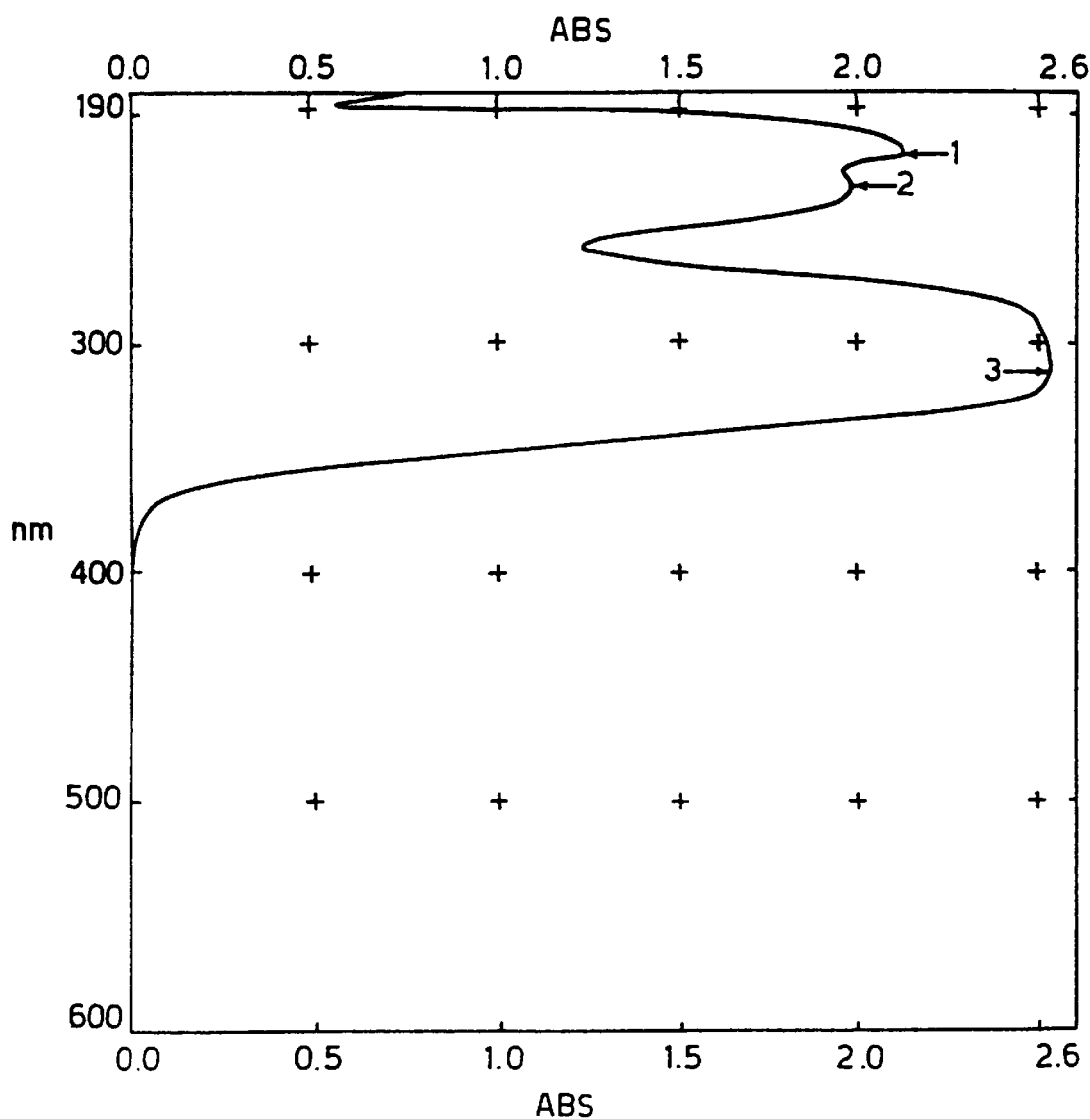
FIG. 4 shows the ultraviolet spectrum of SOLTAN™ with added caffeic acid produced in accordance with Example 1.

A comparison of the spectra of FIGS. 3 and 4 clearly shows that addition of caffeic acid to SOLTAN improves the uv absorbence of the composition remarkably, particularly at 320 nm.

EXAMPLE 4

Figure 5:
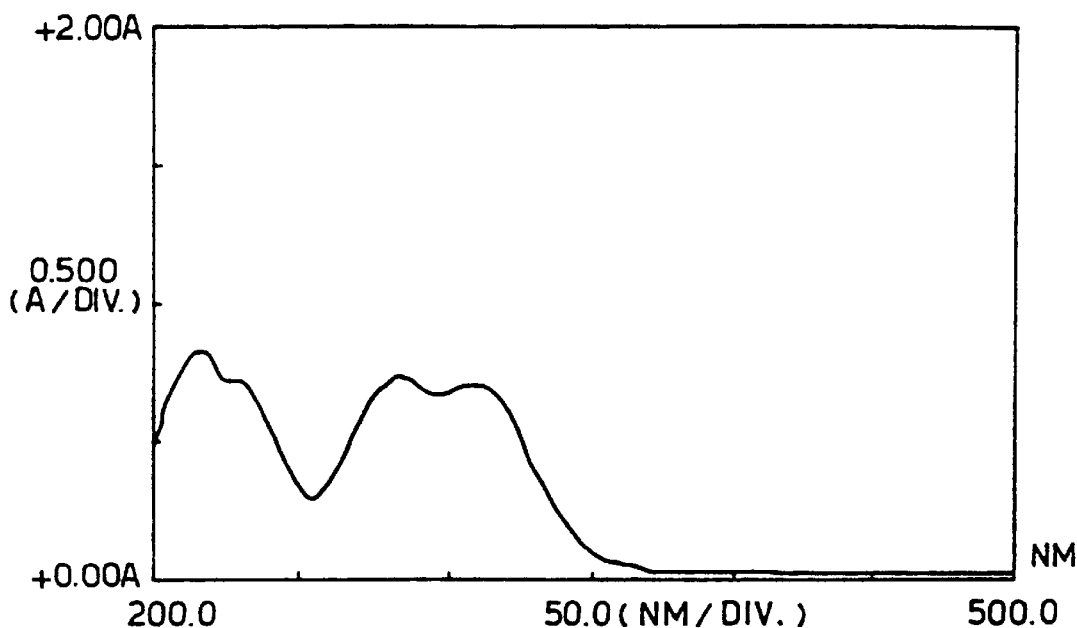
FIG. 5 shows the ultraviolet spectrum of dimethoxycinnamic acid.

The uv absorption of dimethoxycinnamic acid, a compound found in barley and closely related to caffeic acid and its derivatives, was ascertained as shown in FIG. 5. As has been discussed previously, dimethoxycinnamic acid is a strong absorber in both uvA and uvB.

The methyl ester of dimethoxycinnamic acid was manufactured for investigation in the following manner.

3,4-Dimethoxycinnamic acid (5 g) was added to freshly distilled thionyl chloride (70 ml) and dry benzene (50 ml), and the mixture was boiled under reflux for 1 hour. The excess thionyl chloride was removed by repeated evaporation from benzene under vacuum. The unpurified acid chloride was then resuspended in benzene and added to methanol (50 ml), and the mixture was boiled under reflux for 40 mins. The cooled mixture was added to 1M NaHCO$_3$ solution (100 ml) and mixed with careful release of pressure. The organic phase was removed and washed again with 1M NaHCO$_3$ solution (4×100 ml), dried over Na2SO4 (anhydrous) and evaporated to dryness under vacuum. The resultant solid was recrystallised from ethanol to give methyl dimethoxycinnamate as beige crystals in 82% yield. mp 51–53° C.

The UV spectrum of this material when measured as a 0.001% solution in ethanol exhibited a $\lambda_{max}$ of 295 nm; m.a.v. of 13875; $E^{1Z}_{1cm}$ of 625 and also $\lambda_{max}$ of 323 nm; m.a.v. of 16628; $E^{1z}_{1cm}$ of 749.

Figure 6:
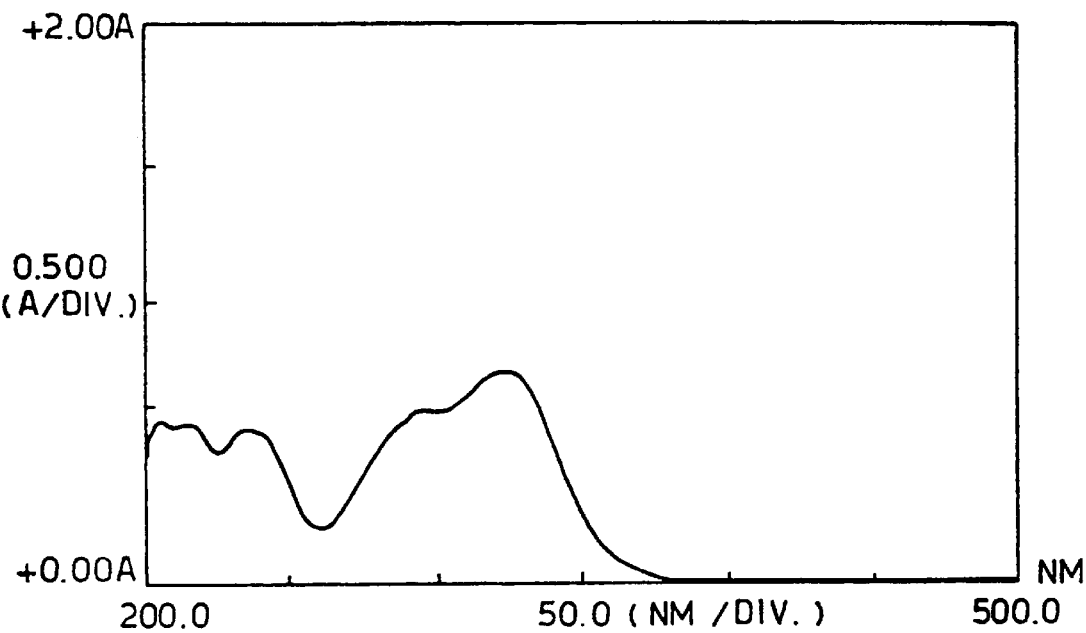
FIG. 6 shows the ultraviolet spectrum of the methyl ester of dimethoxycinnamic acid.

FIG. 6 shows the absorption spectrum of the methyl ester of DMCA, showing, once again, strong absorption in the uvA and uvB regions.

EXAMPLE 5

Steps were taken to prepare the phenyl ester of dimethoxycinnamic acid. This ester was prepared by the same protocol as in Example 4 but using phenol acting as the alcohol. The resulting tan solid was re-crystallized from ethanol to yield pale-tan, odourless crystals in 51% yield. mp 109–111° C.

The UV spectrum of this material when measured as a 0.001% solution in ethanol exhibited a $\lambda_{max}$ of 300 nm; m.a.v. of 15989; $E^{1Z}_{1cm}$ of 263 and also $\lambda_{max}$ of 328 nm; m.a.v. of 21044; $E^{1Z}_{1cm}$ of 741.

Figure 7:
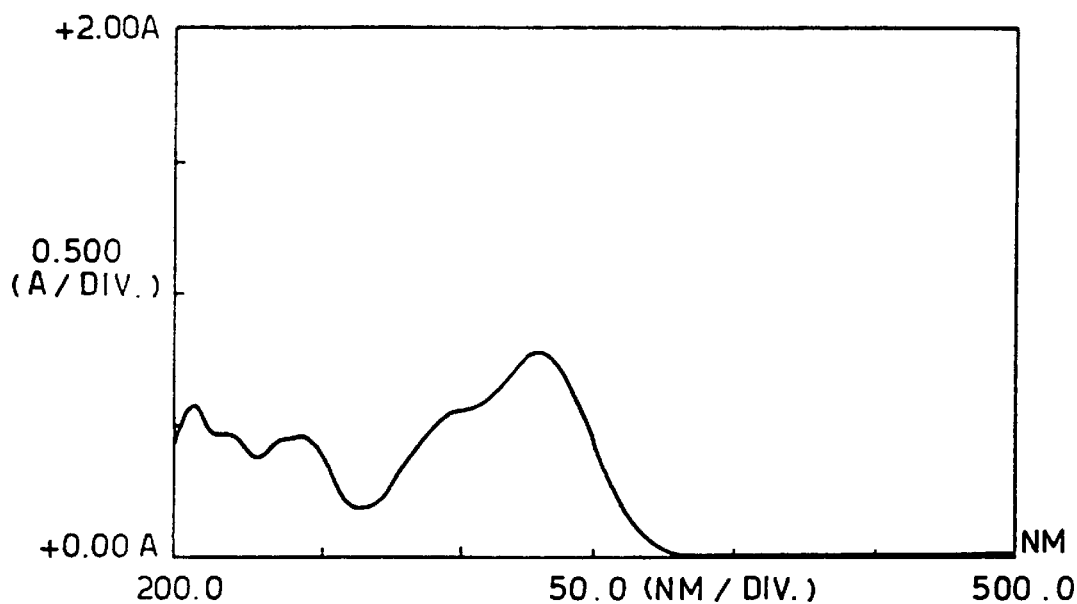
FIG. 7 shows the ultraviolet spectrum of the phenyl ester of dimethoxycinnamic acid.

FIG. 7 shows the absorption spectrum of this ester, once again having strong absorbence in both the uvA and the uvB regions.

EXAMPLE 6

The hexyl ester of the dimethoxycinnamic acid was prepared using the same process as in Example 4 but with hexanol used as the alcohol in this case. An identical washing procedure was used to recover crude hexyl dimethoxy cinnamate as a brown oil in a 79% yield.

The UV spectrum of this material when measured as a 0.001% solution in ethanol exhibited a $\lambda_{max}$ of 295 nm; m.a.v. of 15184; $E^{1Z}_{1cm}$ of 520 and also $\lambda_{max}$ of 322 nm; m.a.v. of 18221; $E^{1Z}_{1cm}$ of 624.

Figure 8:
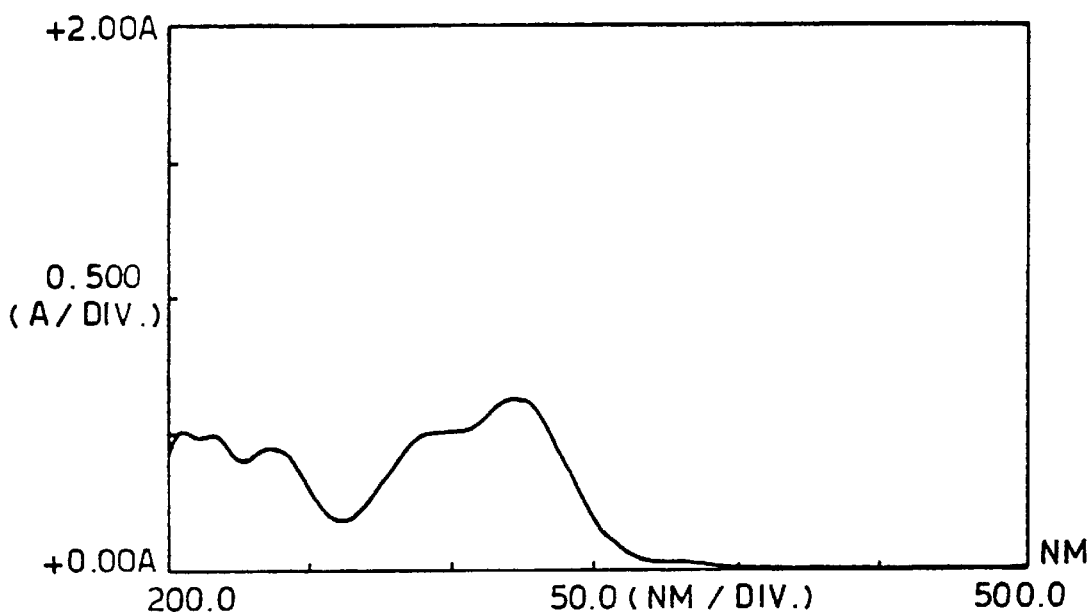
FIG. 8 shows the ultraviolet spectrum of the hexyl ester of dimethoxycinnamic acid.

FIG. 8 shows the uv absorption spectrum of this compound, once again showing good absorption in the uvA and uvB regions.

EXAMPLE 7

Dimethoxyphenyl dimethoxycinnamate was prepared using the process of Example 4 but using 3,4-dimethoxyphenyl acting as the alcohol. The resulting ester was re-crystallised from ethanol to give shiny pink crystals in 43% yield. mp 164° C.

The UV spectrum of this material when measured as a 0.001% solution in ethanol exhibited a $\lambda_{max}$ of 300 nm; $E^{1Z}_{1cm}$ of 492 and also $\lambda_{max}$ of 328.5 nm; $E^{1Z}_{1cm}$ of 672.

This compound has the structure:

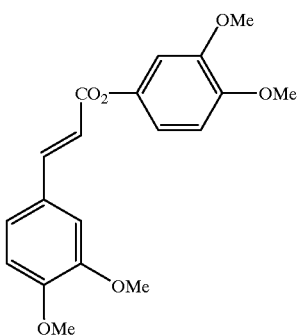

EXAMPLE 8

Phenylethyl dimethoxycinnamate was prepared using the process of Example 4 with phenylethanol acting as the alcohol. The ester was re-crystallised from ethanol to give gold coloured crystals in 45% yield. mp 92–94° C.

The UV spectrum of this material when measured as a 0.001% solution in ethanol exhibited a $\lambda_{max}$ of 295 nm; $E^{1Z}_{1cm}$ of 508 and also $\lambda_{max}$ of 323.5 nm; $E^{1z}_{1cm}$ of 651.

The compound had the structure:

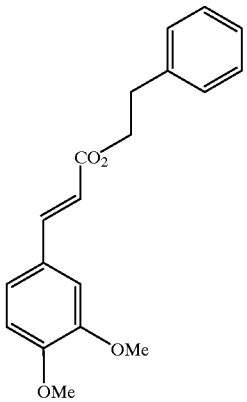

EXAMPLE 9

Ethyl caffeate was prepared as follows. Caffeic acid (1 g) was boiled under reflux in absolute ethanol (30 ml) in the presence of concentrated sulphuric acid (0.5 ml) for two hours. The reaction mixture was then poured into water (100 ml), and then ethyl acetate (100 ml) and 0.1M sodium bicarbonate solution (100 ml) were added. The organic phase was washed successively with 0.1M sodium bicarbonate solution (3×100 ml) and water (2×100 ml) before being dried (sodium sulphate, anhydrous), filtered and evaporated under vacuum to yield a tan coloured crystalline solid. The product was recrystallised from water giving ethyl caffeate as a tan coloured powder in 43% yield. mp 142–143° C.

The UV spectrum of this material when measured as a 0.001% solution in ethanol exhibited a $\lambda_{max}$ of 300 nm; $E^{1Z}_{1cm}$ of 600 and also $\lambda_{max}$ of 331 nm; $E^{1Z}_{1cm}$ of 848.

EXAMPLE 10

The UV spectrum of some of the compounds described can be altered by the addition of materials which are capable of interacting ionically with structural features.

Thus in a 0.001%w/v solution of caffeic acid in ethanol the addition of varying quantities of sodium hydroxide solution results in a shift of the λmax values observed. Addition of 2 molar equivalents of sodium hydroxide gives a significant shift of spectrum into the UVA region. Addition of 3 molar equivalents gives a similar effect with resulting $\lambda_{max}$ values of 304 nm and 345 nm, the 345 nm peak displaying $E=18\times10^3$.

As can be seen, the present invention provides an economic and efficient method of producing caffeic acid and its derivatives in bulk, and, further, provides novel and inventive use of caffeic acid and its derivatives in sunscreen composition.

What is claimed is:

1. A method of manufacturing a compound having the formula:

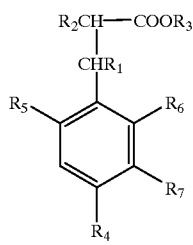

or a salt thereof, wherein $R_1$ is H, OH, or $NH_2$, $R_2$ is H, OH, or $NH_2$, or $R_1$ and $R_2$ form a double bond, $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, and $R_4$, $R_5$ and $R_6$ are each an H or electron donating group and $R_7$ is OH or $OCH_3$, which method comprises reacting chlorogenic acid with a compound of the formula $R_3OH$, wherein $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

2. A method according to claim 1 wherein the enzyme is an esterase, lipase, protease, hydrolase or glycosidase.

3. A method according to claim 1 wherein $R_3$ a hexyl group.

4. A method of treating a plant residue, which method comprises the step of treating the plant residue with a compound of the formula $R_3OH$, wherein $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

5. A method according to claim 4 wherein the enzyme is an esterase, lipase, protease, hydrolase or glycosidase.

6. A method according to claim 4 wherein $R_3$ is a hexyl group.

7. A method according to claim 2 wherein $R_3$ is a hexyl group.

8. A method according to claim 5 wherein $R_3$ is a hexyl group.

9. A method of manufacturing a compound having the formula:

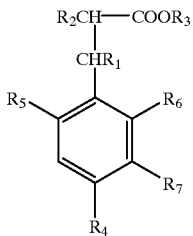

or a salt thereof, wherein $R_1$ and $R_2$ form a double bond, and $R_3$ is a straight or branched chain, substituted or unsubstituted $C_1$–$C_{16}$ alkyl, alkylene, or alkylyne, a substituted or unsubstituted homocyclic aromatic group, $R_4$, $R_5$ and $R_6$ are each an H or electron donating group and $R_7$ is OH or $OCH_3$, which method comprises reacting chlorogenic acid with a compound of the formula $R_3OH$, wherein $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

10. A method according to claim 9 wherein the enzyme is an esterase, lipase, protease, hydrolase or glycosidase.

11. A method according to claim 9 wherein $R_3$ is a hexyl group.

12. A method according to claim 10 wherein $R_3$ is a hexyl group.

13. A method of manufacturing a compound having the formula:

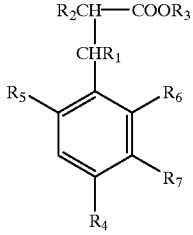

or a salt thereof, wherein $R_1$ and $R_2$ form a double bond, and $R_3$ is a hexyl group, a benzyl group, or a group of the structure $CH_2=CH_2-R_8$ wherein $R_8$ is a straight or branched chain $C_1$–$C_{14}$ alkyl, $R_4$, $R_5$ and $R_6$ are each an H or electron donating group and $R_7$ is OH or $OCH_3$, which method comprises reacting chlorogenic acid with a compound of the formula $R_3OH$, wherein $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

14. A method according to claim 13 wherein the enzyme is an esterase, lipase, protease, hydrolase or glycosidase.

15. A method according to claim 13 wherein $R_3$ is a hexyl group.

16. A method according to claim 14 wherein $R_3$ is a hexyl group.

17. A method of manufacturing a compound having the formula:

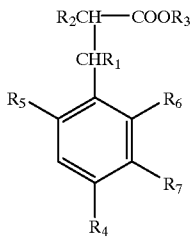

or a salt thereof, wherein $R_1$ is H, OH, or $NH_2$, $R_2$ is H, OH, or $NH_2$, or $R_1$ and $R_2$ form a double bond, $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, and $R_4$, $R_5$ and $R_6$ are H, OH, $NH_2$, $OCH_3$, or a C, to $C_8$ unsaturated alkyl groups, and $R_7$ is OH or $OCH_3$, which method comprises reacting chlorogenic acid with a compound of the formula $R_3OH$, wherein $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

18. A method according to claim 17 wherein the enzyme is an esterase, lipase, protease, hydrolase or glycosidase.

19. A method according to claim 17 wherein $R_3$ is a hexyl group.

20. A method according to claim 18 wherein $R_3$ is a hexyl group.

21. A method of manufacturing a compound having the formula:

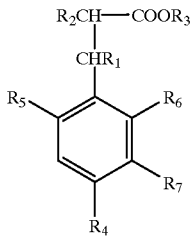

or a salt thereof, wherein $R_1$ and $R_2$ form a double bond, $R_3$ is a straight or branched chain, substituted or unsubstituted $C_1$–$C_{16}$ alkyl, alkylene, or alkylyne, a substituted or unsubstituted homocyclic aromatic group, and $R_4$, $R_5$ and $R_6$ are H, OH, $NH_2$, $OCH_3$ or a C, to $C_8$ unsaturated alkyl group, and $R_7$ is OH or $OCH_3$, which method comprises reacting chlorogenic acid with a compound of the formula $R_3OH$, wherein $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

22. A method according to claim 21 wherein the enzyme is an esterase, lipase, protease, hydrolase or glycosidase.

23. A method according to claim 21 wherein $R_3$ is a hexyl group.

24. A method according to claim 22 wherein $R_3$ is a hexyl group.

25. A method of manufacturing a compound having the formula:

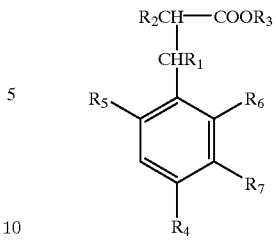

or a salt thereof, wherein $R_1$ and $R_2$ form a double bond, $R_3$ is a hexyl group, a benzyl group, or a group of the structure $CH_2=CH_2-R_8$ wherein $R_8$ is a straight or branched chain $C_1$–$C_{14}$ alkyl, and $R_4$, $R_5$ and $R_6$ are H, OH, $NH_2$, $OCH_3$ or a C, to $C_8$ unsaturated alkyl group, and $R_7$ is OH or $OCH_3$, which method comprises reacting chlorogenic acid with a compound of the formula $R_3OH$, wherein $R_3$ is a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

26. A method according to claim 25 wherein the enzyme is an esterase, lipase, protease, hydrolase or glycosidase.

27. A method according to claim 25 wherein $R_3$ is a hexyl group.

28. A method according to claim 26 wherein $R_3$ is a hexyl group.

29. A method of preserving the skin of a warm-blooded animal comprising applying to the skin a composition a compound having the formula:

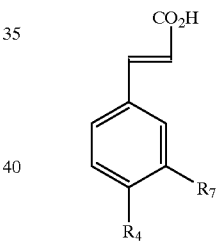

wherein $R_4$ and $R_7$ are each $OCH_3$.

30. A method according to claim 29 wherein the preservation is by preventing uv light damage.

31. A method of manufacturing caffeic acid derivatives, which method comprises reacting chlorogenic acid with a compound of the formula $R_3OH$, wherein $R_3$ is a $C_1$ to $C_{16}$ alkyl, alkylene or alkylyne, or an aromatic group, in the presence of an esterifying enzyme.

32. A method according to claim 31 wherein the reaction takes place in an organic solvent.

33. A method according to claim 31 wherein $R_3$ is a $C_1$ to $C_{16}$ alkyl, alkylene or alkylyne, or an aromatic group.

34. A method according to claim 31 wherein the enzyme is an esterase, lipase, protease, hydrolase or glycosidase.

35. A method according to claim 34 wherein the enzyme is selected from lipase AP6 (Amino), lipase F4, *A. niger* lipase, porcine pancreatic lipase, *C. antarctica* lipase, porcine liver esterase, chymotrypsin and cellulases.

36. A method according to claim 20 wherein $R_3$ is a hexyl group.

37. A method of treating a plant residue to manufacture caffeic acid derivatives, which method comprises the step of treating the plant residue with a compound of the formula $R_3OH$, wherein $R_3$ is a $C_1$ to $C_{16}$ alkyl, alkylene or alkylyne, or an aromatic group, in the presence of an esterifying enzyme.

38. A method according to claim 37 wherein the enzyme is an esterase, lipase, protease, hydrolase or glycosidase.

39. A method according to claim 37 wherein the enzyme is selected from lipase AP6 (Amino), lipase F4, *A. niger* lipase, porcine pancreatic lipase, *C. antarctica* lipase, porcine liver esterase, chymotrypsin and cellulases.

40. A method according to claim 37 wherein $R_3$ is a hexyl group.

41. A method according to claim 37 further comprising the step of solvent extraction of the caffeic acid derivatives.

42. A method according to claim 37 wherein the plant residue is derived from sunflowers.

43. A method according to claim 37 wherein the plant residue is derived from olives.

44. A sunscreen composition comprising:
a) a compound having the formula:

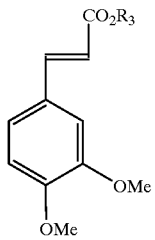

wherein $R_3$ is a $C_1$ to $C_{16}$ alkyl, alkylene or alkylyne, or an aromatic group; and
b) an adjuvant.

45. A method of preserving the skin of a warm-blooded animal comprising:
applying to the skin a composition, the composition having the formula:

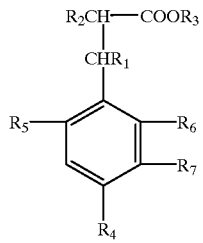

or a salt thereof, wherein $R_1$ is H, OH, or $NH_2$, $R_2$ is H, OH, or $NH_2$, or $R_1$ and $R_2$ form a double bond, $R_3$ is H, a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, and $R_4$, $R_5$ and $R_6$ are each an H or electron donating group and $R_7$ is OH or $OCH_3$, which method comprises reacting chlorogenic acid with a compound of the formula $R_3OH$, wherein $R_3$ is H, a straight or branched chain, substituted or unsubstituted $C_1$–$C_{16}$ alkyl, alkylene, or alkylyne, a substituted or unsubstituted homocyclic or heterocyclic aromatic group, or a group having a uv extinction coefficient of 2,000 or more, in the presence of an esterifying enzyme.

46. A method according to claim 45 wherein the preservation is by preventing uv light damage.

* * * * *